United States Patent [19]

Goldblatt et al.

[11] 4,248,622

[45] Feb. 3, 1981

[54] DERIVATIVES OF 9-FLUORENONE AND THE USE THEREOF AS HERBICIDE

[75] Inventors: Andre J. Goldblatt, Brussels; Andre J. Gillet, Gembloux; Luciano Forni, St. Vaast, all of Belgium

[73] Assignee: Chimac Societe Anonyme, Brussels, Belgium

[21] Appl. No.: 118,711

[22] Filed: Feb. 5, 1980

Related U.S. Application Data

[63] Continuation of Ser. No. 898,575, Apr. 21, 1978, abandoned.

[51] Int. Cl.³ .............................................. A01N 33/06
[52] U.S. Cl. ........................................ 71/121; 564/427
[58] Field of Search ................................. 71/121, 123

[56] References Cited

U.S. PATENT DOCUMENTS

| | | | |
|---|---|---|---|
| 2,653,864 | 9/1953 | Schlesinger | 71/123 |
| 3,393,240 | 7/1968 | Muller et al. | 71/121 |

*Primary Examiner*—Catherine L. Mills
*Attorney, Agent, or Firm*—Sughrue, Rothwell, Mion, Zinn and Macpeak

[57] ABSTRACT

This invention relates to new derivatives of 1-amino-fluoren-9-one and to the use thereof, particularly as herbicides.

The new derivatives are 1-amino-fluoren-9-ones substituted in position 1 by a dialkylamino radical or a nitrogenous heterocyclic ring and possibly also substituted in at least one other position by a halogen atom, a trihalogenomethyl radical, a trifluoromethylsulfonyl radical and/or a nitro radical.

3 Claims, No Drawings

DERIVATIVES OF 9-FLUORENONE AND THE USE THEREOF AS HERBICIDE

This is a continuation of application Ser. No. 898,575, filed Apr. 21, 1978, now abandoned.

BRIEF DESCRIPTION OF THE INVENTION

This invention relates to new derivatives of 1-amino-fluoren-9-one and to the preparation thereof. It also relates to new preemergence herbicidal compositions containing at least one new derivative of 1-amino-fluoren-9-one.

The new derivatives of 1-amino-fluoren-9-one of the present invention may be represented by the following formula:

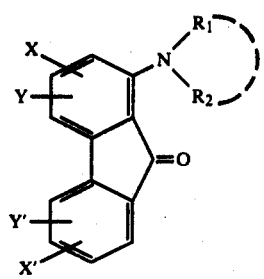
(I)

in which $R_1$ and $R_2$ which may be identical or different represent a lower alkyl, alkenyl or alkynyl radical and may also form with the attached nitrogen atom a heterocyclic ring, whereas one or two of the symbols $R_1$ and $R_2$ may also represent hydrogen, X and X' which may be identical or different represent hydrogen, a halogen atom such as chlorine, bromine or fluorine, a trihalogenomethyl radical, such as trifluoromethyl, trichloromethyl or tribromomethyl radical, or a trifluoromethylsulfonyl ($CF_2SO_2$) radical, and Y and Y' which may be identical or different represent hydrogen or a nitro radical.

Among the new derivatives of 1-amino-fluoren-9-one of formula I, the following may be cited:
1-dimethylamino-2-fluoro-fluoren-9-one;
1-amino-2-fluoro-fluoren-9-one;
1-dimethylamino-4-fluoro-fluoren-9-one;
1-methylamino-4-fluoro-fluoren-9-one;
1-amino-4-fluoro-fluoren-9-one;
1-dimethylamino-7-fluoro-fluoren-9-one.

PREPARATION OF THE COMPOUNDS OF FORMULA I

This invention also relates to the preparation of the new derivatives of 1-amino-fluoren-9-one of formula I.

When, in the formula I, $R_1$ and $R_2$ represent an alkyl, alkenyl or alkynyl radical, the compounds of formula I may be prepared by reacting a 1-amino-fluoren-9-one of the following formula:

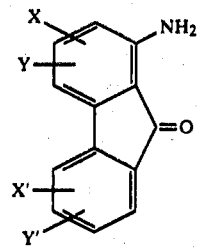
(II)

in which X, X', Y and Y' have the above meanings, with an alkylating, alkenylating or alkynylating reagent.

For example, when it is desired to obtain a compound of formula I, in which $R_1$ and $R_2$ represent the same alkyl radical whereas X, X', Y and Y' have the above meanings, the compound of formula II may be reacted with an alkyl p-toluene sulfonate or a dialkyl sulfate.

When, in the compounds of formula I, $R_1$ represents hydrogen and $R_2$ represents a lower alkyl, alkenyl or alkynyl radical, the compounds of formula I may also be prepared by reacting a compound of the following formula:

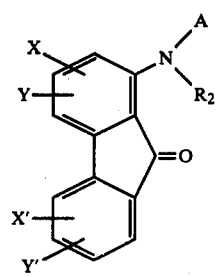
(III)

in which $R_2$ represents a lower alkyl, alkenyl or alkynyl radical, X, X', Y and Y' have one of the above meanings and A represents an alkanoyl group such as an acetyl group, an alkoxycarbonyl group or a toluene-sulfonyl (tosyl) group, with sulfuric acid.

It has been found that the compounds of formula I have remarkable preemergence herbicidal properties.

This invention therefore relates also to the preemergence herbicidal compositions containing an effective amount of at least one compound of formula I.

The herbicidal compositions according to this invention may be solid or liquid formulations consisting of at least one compound of formula I and an inert carrier or conventional formulation adjuvant.

Preparation of said compositions broadly involves admixing an effective amount of the herbicidal agent of formula I and adjuvant.

Use of said compositions broadly involves application of an effective amount of said compounds of formula I or preferably said herbicidal compositions to the soil containing seeds of the plants to be controlled.

Typical formulations include, for instance, dusts, wettable powders, granules, emulsionable concentrates, free flowable concentrates and the like.

Dusts are generally prepared by grinding together from about 2% to 98% by weight of at least one active material of formula I with from about 98% to 2% by weight of a solid diluent, such as attaclay, kaolin, diatomaceous earth, fullers earth, silica, talc, pumice, or the like.

Granular formulations may be prepared by applying a liquid solution or suspension of the active material to sorptive granular carriers, such as attaclay, kaolin or diatomite granules. Alternatively, they may be mixed with inert carriers and applied to non-sorptive granules, such as sand or limestone.

Wettable powders are prepared by grinding at least one active ingredient of formula I with a solid carrier, such as used in the dust formulation.

In addition to the solid carriers, the wettable powders also contain a dispersing agent and/or a surfactant or wetting agent, such as sodium lignosulfonate and/or a condensate of polyoxyethylene with an alcohol or an alkylphenol, namely nonylphenol.

The wettable powders are usually dispersed in water and applied as a liquid spray to the area or locus where control of undesirable plant species is desired.

The emulsionable concentrate is prepared by dissolving a compound of formula I in a liquid carrier such as a mixture of xylenes containing a surfactant and a wetting agent such as calcium dodecylbenzenesulfonate and a condensate of polyoxyethylene with an alcohol or an alkylphenol, namely nonylphenol.

The emulsionable concentrate is usually dispersed in water and applied as a liquid spray to the area or locus where control of undesirable plant species is necessary.

For use as preemergence herbicides, the dusts or liquid sprays containing the active compound of formula I can be applied to the soil shortly prior to or after planting or very shortly after the emergence of weeds. In some cases, the active herbicidal compounds of formula I could be advantageously used in mixture with known herbicides.

This invention also relates to a method for the preemergence control of undesirable plant species, said method consisting in applying to soil containing seeds of said undesirable plant species a herbicidally effective amount of at least one compound of formula I. The effective amount of said compounds is of about 0.5 to 6 kg/hectare, preferably about 2.5 kg/hectare.

EXAMPLES

The preparation of the new compounds of formula I is represented by the following reaction scheme and illustrated by the following non-limitative examples 1 to 9.

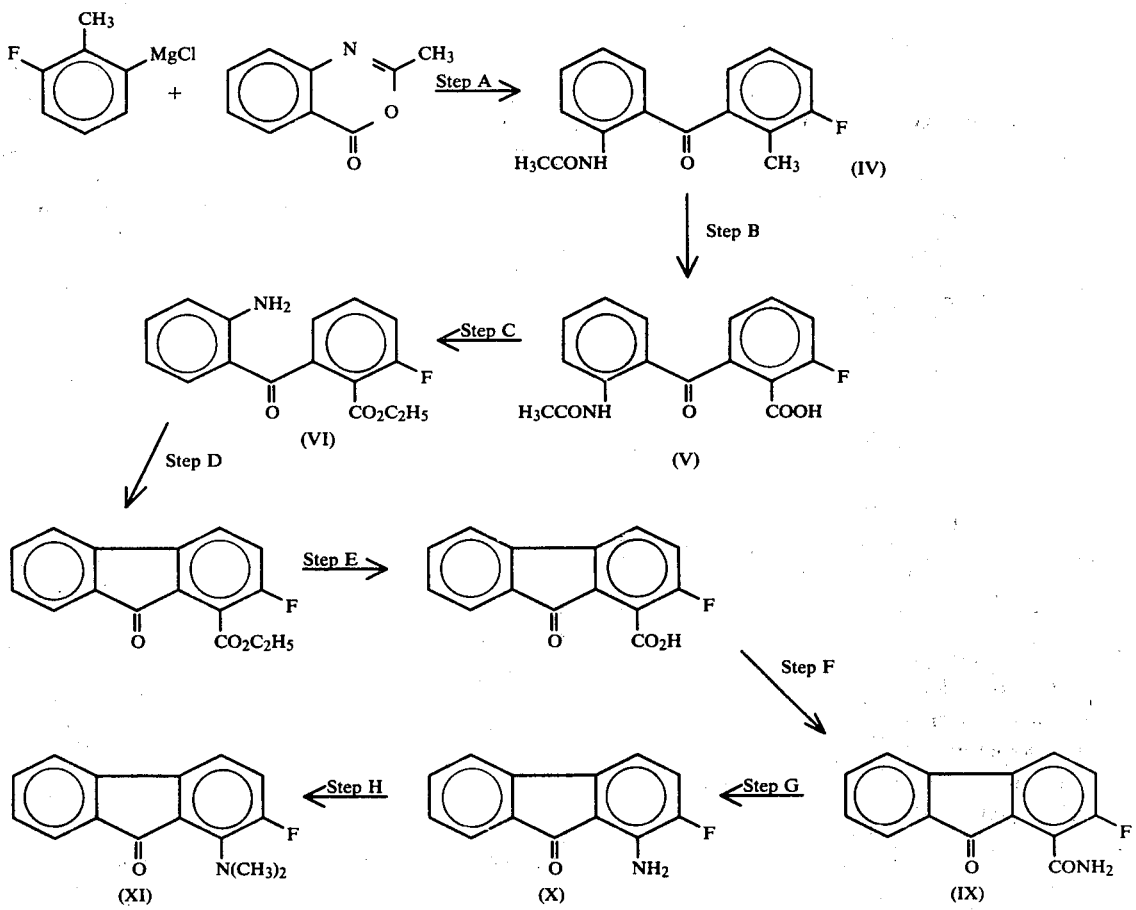

The identification characteristics of the various compounds disclosed in the examples have been obtained under the following conditions.

All analyses stand within the normal standards.

Melting points are uncorrected and are measured on a Boetius hot-stage microscope.

IR spectra are measured on a Pye-Unicam SP 1100 spectrophotometer and are recorded from KBr discs.

Mass spectra (MS) are recorded on a Jeol JMS-D 100 MARK II double-focusing mass-spectrometer at 75 eV.

NMR spectra are recorded on a Varian T 60 spectrometer with TMS as internal standard. The solvent is indicated with brackets.

EXAMPLE 1: STEP A 2-methyl-3-fluoro-2'-acetylamino-benzophenone (IV)

10 ml of dry tetrahydrofuran, 0.5 g of Mg and one crystal of iodine are refluxed until complete discoloration of the medium. 0.5 ml of ethyl bromide is added to initiate the reaction.

Then, 2.9 g of 2-chloro-6-fluoro-toluene are added dropwise.

Reflux is maintained until almost all the magnesium is consumed.

After cooling at room temperature, the mixture is filtered in a dropping funnel. The resulting filtrate is added dropwise to a stirred suspension of 3.2 g of acetylanthranil (prepared by the method of L. A. Errede and J. J. McBrady, J. Org. Chem., 42, 3863 (1977)) in 20 ml of dry tetrahydrofuran at −10° C., the temperature being held below −5° C. After the addition is completed, the stirring is continued for ½ hour at −5° C., ¼ hour at 0° C. and one hour at room temperature.

The mixture is cooled to −10° C. and 25 ml of HCl 2N are added dropwise, the temperature being maintained below 0° C. The resulting suspension is extracted three times with 50 ml of ether. The combined ethereal extracts are washed once with 20 ml of NaOH 0.5N, twice with water, dried on $MgSO_4$ and evaporated to dryness. The resulting oil is extracted with hexane. Upon evaporation of the solvent, the product crystallises: Yield 33% (m.p.: 113°–114° C.).

I.R.: $\nu_{CO}=1695$ cm$^{-1}$.

NMR: (CDCl$_3$): CH$_3$: doublet—2.20δ—3H; COCH$_3$: singlet—2.30δ—3H; NH: broad—11.5δ—1H.

MS: M.+ = m/e 271

EXAMPLE 2: STEP B

2'-acetylamino-3-fluoro-benzophenone-2-carboxylic acid 1 g of 2-methyl-3-fluoro-2'-acetylamino-benzophenone is added to a refluxing solution of 1 g of $MgSO_4$ in 50 ml of water. 2 g of $KMnO_4$ are added portionwise. The reflux is maintained for 5 hours. While hot, the mixture is filtered and the filtrate acidified with HCl 2N and left cooling to room temperature. The resulting crystals are filtered and dried. Yield: 39% (m.p.: 178.5°–180° C.).

IR: $\nu_{CO}=1715$ cm$^{-1}$.

NMR: (DMSO-d$_6$): COCH$_3$: singlet—2.05δ—3H; COOH: broad—10.50δ—1H (exchanges with D$_2$O).

MS: M.+ = m/e 301.

EXAMPLE 3: STEP C

Ethyl-2'-amino-3-fluoro-benzophenone-2-carboxylate (VI)

16 g of 2'-acetylamino-3-fluoro-benzophenone-1-carboxylic acid are dissolved in a saturated solution of HCl gas in absolute ethanol. The mixture is heated 20 h. at 40° C.

After cooling, the excess alcohol is evaporated under vacuum. The residual oil is dissolved in chloroform, washed three times with 50 ml of NaOH 1N and once with water.

The dried organic layer is evaporated to dryness. The ester is obtained as an oil that crystallises slowly. The crystals are recrystallized from cyclohexane. Yield 98% (m.p.: 85°–86° C.).

IR: $\nu_{CO}=1720$ & 1725 cm$^{-1}$; $\nu_{NH}=3360$–3480 cm$^{-1}$.

NMR: (CDCl$_3$): CH$_2$CH$_3$: triplet—1.10δ—3H; CH$_2$CH$_3$: quadruplet—4.12δ—2H; NH$_2$: singlet—4.6-5δ—1H(exchanges with D$_2$O).

MS: M.+ = m/e 287.

EXAMPLE 4: STEPS D, E, F and G 1-amino-2-fluoro-fluoren-9-one (X)

All the following steps may be performed without purification of the intermediate products. Global yield of the steps D to G is 15.4%.

(a) Ethyl 2-fluoro-fluoren-9-one-1-carboxylate (VII)

48 g of ethyl 2'-amino-3-fluoro-benzophenone-2-carboxylate are dissolved in 840 ml of $H_2SO_4$ 50% and cooled to −5° C. A saturated solution of 13.7 g of NaNO$_2$ in water is added dropwise, maintaining the temperature at −5° C. After the addition is completed, the solution is stirred ½ hour, at 0° C., one hour at room temperature and finally two days at 50° C. A yellow precipitate forms slowly. The mixture is poured on 1 l. of water. The resulting solid is filtered and washed with water until neutrality of the filtrate is achieved. The characteristics of the pure product isolated from column chromatography on silica gel (eluant: CHCl$_3$) are the following:

m.p. 122°–123° C.

IR: $\nu_{CO}$: 1715 and 1730 cm$^{-1}$.

NMR: (CDCl$_3$): CH$_2$CH$_3$: triplet—1.45δ—3H; CH$_2$CH$_3$: quadruplet—4.55δ—2H.

MS: M.+ = m/e 270.

(b) 2-fluoro-fluoren-9-one-1-carboxylic acid (VIII)

The ethyl 2-fluoro-fluoren-9-one-1-carboxylate is mixed with 500 ml of NaOH 6N and refluxed for 2 hours. After cooling, the mixture is diluted with twice its volume of water and acidified with concentrated HCl. The yellow precipitate that forms is filtered and washed with water. The melting point of the pure product isolated from column chromatography on silica gel (eluant: CHCl$_3$/CH$_3$CO$_2$C$_2$H$_5$ 3/1) is: 209.210° C.

(c) 2-fluoro-fluoren-9-one-1-carboxamide (IX)

The well-dried 2-fluoro-fluoren-9-one-1-carboxylic acid is refluxed 2 hours with 500 ml of SOCl$_2$. After reaction, the excess of SOCl$_2$ is evaporated under vacuum, the last traces of the reactant being eliminated by azeotropic distillation twice with benzene. The resulting solid is dissolved in 300 ml of dry benzene and 200 ml of concentrated NH$_4$OH are added. Upon stirring at room temperature, a yellow precipitate appears. The stirring is maintained for 2 hours. The solid is filtered and washed with water until the filtrate is neutral. The product, recrystallized from acetic acid, has the following melting point: 220° C. (dec).

(d) 1-amino-2-fluoro-fluoren-9-one (X)

The 2-fluoro-fluoren-9-one carboxamide is added portionwise to 165 ml of a solution of NaOBr at 0° C. (obtained by the reaction of 5 ml of Br$_2$ and 160 ml of NaOH 3N).

The mixture is stirred 15 minutes at 0° C. and then at 10° C. until a clear solution is obtained. The solution is then heated stepwise to 80° C. A yellow precipitate appears. The heating is maintained until the evolution of gas ceases. The mixture is poured on 200 ml of water. The solid is filtered, washed with water and dried. (m.p. 130°-131° C.).

IR: $\nu_{CO}$: 1695 cm$^{-1}$; $\nu NH_2$: 3350-3450 cm$^{-1}$.
NMR: (CDCl$_3$): NH$_2$: broad—5.55δ—2H (exchanges with D$_2$).
MS: M.$^+$ = m/e 213.

EXAMPLE 5: STEP H 1-dimethyl-amino-2-fluoro-fluoren-9-one (XI)

8 g of 1-amino-2-fluoro-fluoren-9-one are refluxed with stirring with 160 ml of freshly distilled (CH$_3$)$_2$SO$_4$. After completion of the reaction (2 hours), the excess of sulphate is evaporated under vacuum until only an oily residue remains. The oil is poured on 200 ml of water and basified with concentrated NH$_4$OH with vigourous stirring. The solution is extracted exhaustively with CHCl$_3$. The combined organic layers are dried and evaporated to dryness.

8.5 g (93.9%) of an oil crystallises.
m.p. 45°-46° C.
IR: $\nu_{CO}$ = 1695 cm$^{-1}$.
NMR (CDCl$_3$): CH$_3$: double singlet—3.10 and 3.15δ—2×3H
MS: M.$^+$ = m/e 241.

EXAMPLE 6

1-dimethylamino-4-fluoro-fluoren-9-one

This compound has been prepared by the method of the preceeding examples. m.p. 105°-106° C.

EXAMPLE 7

1-methylamino-4-fluoro-fluoren-9-one

This compound has been prepared by a method similar to this used in example 4 giving 1-amino-4-fluoro-fluoren-9-one instead of 1-amino-2-fluoro-fluoren-9-one. m.p. 139°-144° C.

EXAMPLE 8

1-amino-4-fluoro-fluoren-9-one

This compound has been prepared by the methods of examples 1 to 4 starting from 2-chloro-4-fluoro-toluene instead of 2-chloro-6-fluoro-toluene of example 1. m.p. 205°-206° C.

The following examples 9 to 11 illustrate a few herbicidal compositions according to this invention.

EXAMPLE 9

Wettable Powder

Active ingredient of formula I: 50% by weight
Carrier: 50% by weight
The carrier has the following composition:
kaolin speswhite: 42% by weight
colloidal silicic acid: 51% by weight
surfactant: 6% by weight
wetting agent: 1% by weight The kaolin speswhite is sold by the "British Continental China-Clay" (Belgium), the colloidal silicic acid by "Degussa" (West Germany).

The surfactant is a sodium lignosulfonate and the wetting agent a condensate of polyoxyethylene and a fatty alcohol and are manufactured by "Tensia" (Belgium).

EXAMPLE 10

Wettable Powder

Active ingredient of formula I: 50% by weight
Carrier: 50% by weight
The carrier has the following composition:
kaolin speswhite: 92% by weight
surfactant: 6% by weight
wetting agent: 1% by weight
colloidal silicic acid: 1% by weight.

The characteristics of the carrier are the same as in example 9.

EXAMPLE 11

Emulsifiable Concentrate

Concentration: 500 g active ingredient of formula I/liter. 500 g of the active ingredient are dissolved in a liquid carrier and the solution is brought to 1 liter, the liquid carrier having the following composition, for 100 ml:
1 g Tensiofix a.s.
4 g Tensiofix b.s.
xylol to 100 ml.

The Tensiofix a.s. is an anionic surfactant, namely calcium dodecylbenzenesulfonate, and the Tensiofix b.s. is a non-ionic wetting agent, a condensate of polyoxyethylene and nonylphenol. Both are manufactured by "Tensia" (Belgium).

The following examples illustrate the herbicidal activity of the compounds of formula I.

EXAMPLES 12 to 27

The selective preemergence herbicidal activity of the new derivatives of 1-amino-fluoren-9-one of formula I is exemplified by the following tests in which the seeds of several important monocotyledonous and dicotyledonous plants are separately seeded on soil in separate cups. After planting, the cups are sprayed with the selected formulations of examples 9 to 11 containing the test compound. The treated cups are then placed on greenhouse benches, watered and cared for in accordance with conventional greenhouse procedures. Three to six weeks after treatment, the tests are brought to the end and each cup is examined and rated according to a rating system expressing the percentage of injury of the considered species. The herbicidal activity of the active ingredients of the present invention is evident from the test results which are reported in the table I below.

The table gives the doses, expressed in kg of active ingredient per hectare, that has been needed to obtain an eradication of 50% and 90% of the mentioned plant species.

The tests have been performed with 1-dimethylamino-2-fluoro-fluoren-9-one as active ingredient.

TABLE I

| Ex. n° | PLANT SPECIES | DOSES (kg/ha) for eradication larger than | |
|---|---|---|---|
| | | 50% | 90% |
| 12 | Abutilon theophrasti | 2.0 | >4.0 |
| 13 | Amaranthus hybridus | <0.25 | <0.25 |
| 14 | Amaranthus viridis | 0.25 | 0.5-1.0 |
| 15 | Arachis hypogea | >>4.0 | >>>4.0 |
| 16 | Beta vulgaris | <<1.0 | <<1.0 |
| 17 | Brassica napus | <1.0 | 4.0 |
| 18 | Digitaria velutina | <<0.25 | 0.25-0.5 |
| 19 | Eleusine indica | 0.25-0.50 | 1.0 |
| 20 | Gossypium hirsutum | >8.0 | >16.0 |
| 21 | Lolium perenne | 1.0 | >4.0 |

TABLE I-continued

| Ex. n° | PLANT SPECIES | DOSES (kg/ha) for eradication larger than | |
|---|---|---|---|
| | | 50% | 90% |
| 22 | Oryza sativa | >4.0 | >>4.0 |
| 23 | Panicum miliaceum | <1.0 | 1.0-2.0 |
| 24 | Pisum sativum | >>4.0 | >>>4.0 |
| 25 | Setaria faberii | <0.25 | 0.25-0.5 |
| 26 | Sorghum arundinaceum | 0.5-1.0 | >1.0 |
| 27 | Zea mais | >4.0 | >>4.0 |

What we claim is:

1. A method for the preemergence control of weeds comprising applying to soil containing weeds a herbicidal effective amount of a derivative of a fluorinated 1-amino-9-fluorenone of the formula:

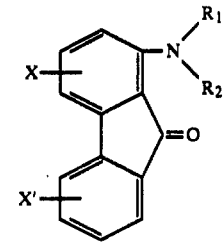

in which one of the symbols X and X' represents a fluorine atom, whereas the other represents hydrogen, and $R_1$ and $R_2$, which may be identical or different, represent hydrogen or a lower alkyl or alkenyl radical.

2. A method for the preemergence control of weeds comprising applying to soil containing weeds a herbicidal effective amount of at least one compound selected from the group consisting of 1-amino-2-fluoro-9-fluorenone and 1-diloweralkyl or alkenylamino-2-fluoro-9-fluorenones.

3. A method for the preemergence control of weeds comprising applying to soil containing weeds a herbicidal effective amount of 1-dimethylamino-2-fluoro-9-fluorenone.

* * * * *